US006124436A

United States Patent [19]

[11] Patent Number: 6,124,436
[45] Date of Patent: Sep. 26, 2000

McClanahan et al.

[54] PURIFIED MAMMALIAN MONOCYTE ANTIGENS AND RELATED REAGENTS

[75] Inventors: Terrill K. McClanahan, Sunnyvale; Daniel M. Gorman, Newark; Laurel M. Bolin, San Jose, all of Calif.

[73] Assignee: Schering Corporation, Kenilworth, N.J.

[21] Appl. No.: 08/600,430

[22] Filed: Feb. 13, 1996

[51] Int. Cl.$^7$ .............................. C07K 16/00; C12N 5/00; G01N 33/563

[52] U.S. Cl. ...................................... 530/387.1; 530/387.9; 530/391.1; 530/391.3; 530/391.7; 435/240.27; 436/512

[58] Field of Search .............................. 530/387.1, 387.9, 530/391.1, 391.3, 391.7; 435/240.27; 436/512

[56] References Cited

PUBLICATIONS

Welcher et al (PNAS, 1991, 88: 7195–7199).
Takeda (Res Proj in Rev, Nissan Sci Found, 1995, 18: 211–214.
Miyazaki et al (Jap. J. Physiol, 1994, 44: 5236).
Snipes et al (J. Cell Bio, 1992, 117:225–238).
Roitt et al (Immunology, 1993, Mosby, St Louis, p. 6.4–6.5.
Adlkofer, et al. "Hypermyelination and Demyelinating Peripheral Neuropathy in Pmp22–Deficient Mice," *Nature Genetics*, 11:274–280, Nov., 1995.
Gordon, et al. "Molecular Immunobiology of Macrophages: Recent Progress," *Cur. Opinion in Immunol.*, 7:24–33, 1995.
Ignatius, et al. "Lipoprotein Uptake by Neuronal Growth Cones in Vitro," *Science*, 236:959–962, May, 1987.
Linton, et al. "Prevention of Atherosclerosis in Apolipoprotein E–Deficient Mice by Bone Marrow Transplantation," *Science*, 267:1034–1037, Feb., 1995.
Muller et al. "A Specific 37,000–Dalton Protein that Accumulates in Regenerating but not in Nonregenerating Mammalian Nerves," *Science* 228:499–501, Apr., 1985.
Nishinakamura, et al. "Mice Deficient for the IL–3/GM–CSF/IL–5 βc Receptor Exhibit Lung Pathology and Impaired Immune Response, while $\beta_{IL3}$Receptor–Deficient Mice are Normal," *Immunity*, 2:211–222, Mar., 1995.
Suter, et al. "Progress in the Molecular Understanding of Hereditary Peripheral Neuropathies Reveals New Insights into the Biology of the Peripheral Nervous System," *TINS*, 16:50–56, 1993.
Taylor, et al. "Epithelial Membrane Protein–1, Peripheral Myelin Protein 22, and Lens Membrane Protein 20 Define a Novel Gene Family," *J. Biol. Chem.*, 270:28824–28833, Dec., 1995.
Suter, et al. "Peripheral Myelin Protein 22: Facts and Hypotheses," *J. of Neuroscience Research*, 40:145–151, 1995.
Kumar, et al. "Cloning and Expression of a Major Rat Lens Membrane Protein, MP20," *Exp. Eye Res.*, 56:35–43, 1993.
Suter, et al. "Trembler Mouse Carries a Point Mutation in a Myelin Gene," *Nature*, 356:241–244, Mar., 1992.

*Primary Examiner*—Paula K. Hutzell
*Assistant Examiner*—Susan Ungar
*Attorney, Agent, or Firm*—Gerald P. Keleher; Edwin P. Ching

[57] ABSTRACT

Cell surface antigens from mammals, reagents related thereto, including purified proteins, specific antibodies, and nucleic acids encoding said antigens. Methods of using said reagents and diagnostic kits are also provided.

22 Claims, No Drawings

PURIFIED MAMMALIAN MONOCYTE ANTIGENS AND RELATED REAGENTS

FIELD OF THE INVENTION

The present invention relates to compositions, including proteins which function in controlling physiology, development, and differentiation of mammalian cells, e.g., cells of a mammalian immune or neural system. In particular, it provides proteins and mimetics which regulate cellular physiology, development, differentiation, or function of various cell types including monocytes and neuronal cells.

BACKGROUND OF THE INVENTION

The immune system of vertebrates consists of a number of organs and several different cell types. Two major cell types include the myeloid and lymphoid lineages. Among the lymphoid cell lineage are B cells, which were originally characterized as differentiating in fetal liver or adult bone marrow, T cells, which were originally characterized as differentiating in the thymus, and natural killer (NK) cells. See, e.g., Paul (ed.) (1994) *Fundamental Immunology* (3d ed.) Raven Press, New York.

Among the myeloid cell lineage are monocytes, which help mediate the innate immune response. This response includes macrophage-mediated phagocytosis of bacteria, release of inflammatory cytokines, and antigen processing and presentation to T cells.

In many aspects of the development of an immune response or cellular differentiation, soluble proteins, e.g., cytokines, and cell surface antigens, e.g., CD markers, play critical roles in regulating cellular interactions. These cytokines and cell markers mediate cellular activities in many ways. They have been shown, in many cases, to modulate proliferation, growth, and differentiation of hematopoietic stem cells into the vast number of progenitors composing the lineages responsible for an immune response.

However, the cellular molecules which are expressed by different developmental stages of cells in these maturation pathways are still incompletely identified. Moreover, the roles and mechanisms of action of signaling molecules which induce, sustain, or modulate the various physiological, developmental, or proliferative states of these cells are poorly understood. Clearly, the immune system and its response to various stresses have relevance to medicine, e.g., infectious diseases, cancer related responses and treatment, allergic and transplantation rejection responses. See, e.g., Thorn, et al. *Harrison's Principles of Internal Medicine* McGraw/Hill, New York.

Medical science relies, in large degree, on appropriate recruitment or suppression of the immune system in effecting cures for insufficient or improper physiological responses to environmental factors. However, the lack of understanding of how the immune system is regulated or differentiates has blocked the ability to advantageously modulate the normal defensive mechanisms to biological challenges. Medical conditions characterized by abnormal or inappropriate regulation of the development or physiology of relevant cells thus remain unmanageable. The discovery and characterization of specific cytokines and markers, e.g., involved in cell-cell interactions, will contribute to the development of therapies for a broad range of degenerative or other conditions which affect the immune system, hematopoietic cells, as well as other cell types. The present invention provides solutions to some of these and many other problems.

SUMMARY OF THE INVENTION

The present invention is based, in part, upon the discovery of a cDNA clone encoding a protein exhibiting sequence similarity to a protein involved in neuronal function.

The invention embraces isolated genes encoding the proteins of the invention, variants of the encoded proteins, e.g., mutations (muteins) of the natural sequence, polymorphic, allelic, and species variants, fusion proteins, chemical mimetics, antibodies, and other structural or functional analogs. Various uses of these different nucleic acid or protein compositions are also provided.

The present invention provides nucleic acids encoding a mammalian AVE02 protein or fragment thereof; a substantially pure AVE02 or peptide thereof, or a fusion protein comprising AVE02 sequence; and an antibody to an AVE02 protein.

In nucleic acid embodiments, the nucleic acid can comprise a sequence of Table 3 or 4.

In substantially pure AVE02 protein or peptide thereof embodiments, the protein or peptide can be from a primate, including a human; comprise at least one polypeptide segment of Table 3 or 4; or exhibit a post-translational modification pattern distinct from natural AVE02 protein. A further embodiment is a composition comprising such a protein and a pharmaceutically acceptable carrier. A fusion protein may provide an epitope tag, useful, e.g., for purification or detection.

In antibody embodiments, the antigen can be a primate protein, including a human; the antibody is raised against a protein sequence of Table 3 or 4; the antibody is a monoclonal antibody; or the antibody is labeled.

The invention also embraces a kit comprising a substantially pure nucleic acid encoding an AVE02 protein; a substantially pure AVE02 protein, e.g., as a positive control; or an antibody or receptor which specifically binds an AVE02 protein.

Methods for screening for ligands or other proteins which specifically bind to AVE02 are also provided.

The availability of these reagents also provides methods of modulating physiology or development of a cell comprising contacting said cell with an agonist or antagonist of an AVE02 protein. For example, the antagonist might be an antibody against a mammalian AVE02 protein or the cell may be a precursor cell of hematopoietic or neural origin.

DETAILED DESCRIPTION OF THE PREFERRED EMBODIMENTS

OUTLINE

I. General
II. Nucleic Acids
  A. natural isolates; methods
  B. synthetic genes
  C. methods to isolate
III. Purified AVE02 protein
  A. physical properties
  B. biological properties
IV. Making AVE02 protein; Mimetics
  A. recombinant methods
  B. synthetic methods
  C. natural purification
V. Physical Variants
  A. sequence variants, fragments
  B. post-translational variants 1. glycosylation
2. others VI. Functional Variants
- A. analogs; fragments
  1. agonists
  2. antagonists
- B. mimetics
  1. protein
  2. chemicals
- C. species variants VII. Antibodies
- A. polyclonal
- B. monoclonal
- C. fragments, binding compositions VIII. Uses
- A. diagnostic
- B. therapeutic IX. Kits
- A. nucleic acid reagents
- B. protein reagents
- C. antibody reagents X. Methods for Isolating AVE02 Specific Binding Partners

I. General

The present invention provides DNA sequence encoding various mammalian proteins which exhibit properties characteristic of a functionally significant monocyte, neuronal, or Schwann cell. The cDNA sequence exhibits various features which are characteristic of mRNAs encoding physiologically and developmentally important cell markers. See, e.g., Suter, et al. (1993) *Trends in Neurosciences* 16:50–56. The human gene described herein contains an open reading frame encoding a presumptive 163 amino acid protein. The protein is structurally related to members of a family of four transmembrane cell surface proteins. As such, the AVE02 protein cloned herein likely represents one member of a class of related genes.

These proteins are designated AVE02 proteins. The natural proteins should be capable of mediating various physiological responses which would lead to biological or physiological responses in target cells. Initial studies had localized this protein to various hematopoietic cell types. See, e.g., Table 1. Biochemical properties are described in Table 2.

TABLE 1

| Distribution of AVE02 markers. |
|---|
| found on activated macrophages; microglia; Schwann cells |

TABEL 2

| Biochemical Properties of human AVE02 markers. |
|---|
| encodes core polypeptide of about 22 kD<br>2 potential N-linked glycosylation sites<br>20 ser/thr (potential O-linked glycosylation sites)<br>7 cysteines, 3 potential intracellular disulfide bonds<br>4 transmembrane regions (see Table 5)<br>intracellular and extracellular domains between transmembrane segments |

Besides roles in T cell mediated immune responses (described above), cells of the monocyte lineage have been implicated in a wide variety of physiological processes beyond the hematopoietic. See, e.g., Gordon, et al. (1995) *Current Opinion in Immunology* 7:24–33. Recent studies in gene-targeted mice reveal that cells of the monocyte lineage are involved in apoE-mediated clearance of atherosclerotic plaques in blood vessels. Animals lacking apoE display severe hypercholesterolemia and related pathology. See, e.g., Muller, et al. (1985) *Science* 228:499–501; Ignatius, et al. (1987) *Science* 236:959–962; and Linton, et al. (1995) *Science* 267:1034–1037. Monocyte lineage cells are also involved in maintenance of clear alveolar lung space. Animals lacking the macrophage-specific genes GM-CSF or the IL-3 receptor β common chain suffer from pulmonary alveolar proteinosis, an accumulation of proteinaceous surfactant in the lung air spaces. See Nishinakamura, et al. (1995) *Immunity* 2:211–222. These results suggest that monocyte cells are involved in a wide range of heretofore seemingly unrelated physiological systems. It is becoming clear that specialized macrophage cells in different systems are important to maintain normal physiology.

The AVE02 gene is a distant sequence homolog of a peripheral myelin protein gene designated PMP22. The two proteins exhibit about 43% residue identity. See Table 5. Alterations in the structure or expression of the PMP22 gene product can cause the Charcot-Marie-Tooth syndrome, a genetically heterogeneous disorder of the peripheral nervous system. Charcot-Marie-Tooth (CMT) syndrome affects about 1 in 2800 persons. CMT type1A has been linked genetically to a duplication or point mutations of the PMP22 gene on human chromosome 17. Other point mutations and duplications in PMP22 can cause Dejerine-Sottas disease and hereditary pressure palsies. Both of these peripheral neuropathies result from loss of function of the Schwann cell's ability to myelinate peripheral motor and sensory axons. Two other forms of CMT, CMT1B and CMTX, result from point mutations in the genes $P_0$ and connexin32, which encode proteins essential to membrane-membrane interactions. All three of these gene products are apparently exclusively expressed by Schwann cells in the peripheral nervous system (PNS) and are necessary for membrane-membrane interactions that permit compact myelin sheath formation. The myelin sheath is essential for axon signal transduction from the periphery to the central nervous system (CNS). Not all of the loci and genes that cause CMT have been determined.

PMP22 is an integral membrane protein with four membrane spanning domains. See, e.g., Adlkofer, et al. (1995) *Nature Genetics* 11:274–280; and Taylor, et al. (1995) *J. Biol. Chem.* 270:28824–28833. These membrane spanning domains are the segments most similar to AVE02, and it is to these domains that point mutations resulting in CMT1A have been mapped. These point mutations occur in amino acids that are conserved between PMP22 and AVE02. It is presumed that mutations in the transmembrane portions disrupt putative homophilic interactions of the protein, as has been shown with the $P_0$ mutations. Expression of PMP22 has been shown to be exclusive to Schwann cells in the PNS and motoneurons in the CNS. AVE02 is expressed by macrophage, T-cells, Schwann cells and the specialized macrophage of the CNS, the microglia. AVE02 is also detected in spleen and thymus. This may suggest that the protein serves a role in response to activation.

PMP22 was discovered in a regeneration experimental paradigm. As a Schwann cell myelin protein, it is highly expressed in normal peripheral nerve but is sharply downregulated in an injury model of the sciatic nerve. In contrast, AVE02 is not normally expressed in adult peripheral nerve, but is induced immediately after a crush injury and remains elevated at least though early regeneration of the axon initial remyelination. This elevation may continue long thereafter. Thus, the homologs PMP22 and AVE02 are inversely regulated in the peripheral nervous system in response to demyelinating events. There is ample evidence that macrophage produced factors such as apolipoprotein E and IL-1 directly signal Schwann cell function in the regenerating nerve. AVE02 may influence Schwann cell recovery by direct membrane protein interactions.

The elevation of AVE02 appears to be a localized effect in the nervous system induced by disruption of the anatomical structure of the nerve. Crush, where regeneration requires axon regrowth and remyelination, induces a sustained elevation of AVE02 expression. Less dramatic disruption of the nerve structure results in a rapid but transient induction of AVE02. This suggests that AVE02 plays a role in neuronal regeneration, and may also be important in neural development.

II. Nucleic Acids

Table 3 discloses the nucleotide and amino acid sequences of one protein of the AVE02 family. The described nucleotide sequences and the related reagents are useful in constructing a DNA clone useful for expressing AVE02 protein, or, e.g., isolating a homologous gene from another natural source, including other members of the family. Typically, the sequences will be useful in isolating other genes, e.g., polymorphic or allelic variants or alternatively spliced isoforms, from human.

The coding sequence runs from nucleotide positions 1 to the codon before the termination codon, 492. See Table 3.

TABLE 3

Nucleotide sequence encoding a human AVE02 protein and predicted amino acid sequence. Also can use complementary nucleic acid sequences for many purposes. Designated SEQ ID NO: 1 and 2.

| | | |
|---|---|---|
| 1 | ATGTCACTCCTCTTGCTGGTGGTCTCAGCCCTTCACATCCTCATTCTTATACTGCTTTTC | 60 |
| 1 | MetSerLeuLeuLeuLeuValValSerAlaLeuHisIleLeuIleLeuIleLeuLeuPhe | 20 |
| 61 | GTGGCCACTTTGGACAAGTCCTGGTGGACTCTCCCTGGGAAAGAGTCCCTGAATCTCTGG | 120 |
| 21 | ValAlaThrLeuAspLysSerTrpTrpThrLeuProGlyLysGluSerLeuAsnLeuTrp | 40 |
| 121 | TACGACTGCACGTGGAACAACGACACCAAAACATGGGCCTGCAGTAATGTCAGCGAGAAT | 180 |
| 41 | TyrAspCysThrTrpAsnAsnAspThrLysThrTrpAlaCysSerAsnValSerGluAsn | 60 |
| 181 | GGCTGGCTGAAGGCGGTGCAGGTCCTCATGGTGCTCTCCCTCATTCTCTGCTGTCTCTCC | 240 |
| 61 | GlyTrpLeuLysAlaValGlnValLeuMetValLeuSerLeuIleLeuCysCysLeuSer | 80 |
| 241 | TTCATCCTGTTCATGTTCCAGCTCTACACCATGCGACGAGGAGGTCTCTTCTATGCCACC | 300 |
| 81 | PheIleLeuPheMetPheGlnLeuTyrThrMetArgArgGlyGlyLeuPheTyrAlaThr | 100 |
| 301 | GGCCTCTGCCAGCTTTGCACCAGCGTGGCGGTGTTTACTGGCGCCTTGATCTATGCCATT | 360 |
| 101 | GlyLeuCysGlnLeuCysThrSerValAlaValPheThrGlyAlaLeuIleTyrAlaIle | 120 |
| 361 | CACGCCGAGGAGATCCTGGAGAAGCACCCGCGAGGGGGCAGCTTCGGATACTGCTTCGCC | 420 |
| 121 | HisAlaGluGluIleLeuGluLysHisProArgGlyGlySerPheGlyTyrCysPheAla | 140 |
| 421 | CTGGCCTGGGTGGCCTTCCCCCTCGCCCTGGTCAGCGGCATCATCTACATCCACCTACGG | 480 |
| 141 | LeuAlaTrpValAlaPheProLeuAlaLeuValSerGlyIleIleTyrIleHisLeuArg | 160 |
| 481 | AAGCGGGAGTGA | 492 |
| 161 | LysArgGlu | 163 |

The CMT phenotype is that of demyelination in the PNS, and leads to eventual loss of axon function causing muscle atrophy. A possible contribution of AVE02 to this phenotype is through a persistent mitogenic signal to Schwann cells, which are known to proliferate in response to axon degeneration, e.g., demyelination.

Particularly preferred embodiments are the sequence corresponding to amino acids 56 to 163, and fragments thereof.

The mouse coding sequence runs from nucleotide positions 1 to 492. See Table 4. Sequence alignments of the human AVE02, mouse AVE02, human PMP22, and mouse PMP22 proteins are presented in Table 5.

TABLE 4

Nucleotide sequence designated SEQ ID NO:3, encoding a mouse AVE02 protein and predicted amino acid sequence designated SEQ ID NO:4. Also can use complementary nucleic acid sequences for many purposes.

| | | |
|---|---|---|
| 1 | ATGTCACTCCTCCTGTTGGTGGTCTCTGCCCTCCACATCCTCATTCTTGTCTTGCTTTTT | 60 |
| 1 | MetSerLeuLeuLeuLeuValValSerAlaLeuHisIleLeuIleLeuValLeuLeuPhe | 20 |
| 61 | GTGGCCACTTTGGACAAGTCCTGGTGGACTCTCCCAGACAAAGAGTCCCTGAACCTGTGG | 120 |
| 21 | ValAlaThrLeuAspLysSerTrpTrpThrLeuProAspLysGluSerLeuAsnLeuTrp | 40 |

TABLE 4-continued

Nucleotide sequence designated SEQ ID NO:3, encoding a mouse AVE02 protein and predicted amino acid sequence designated SEQ ID NO:4. Also can use complementary nucleic acid sequences for many purposes.

```
121  TATGACTGCACGTGGAACACCACCACTCAAACATGGGCCTGCAGTAACGTCAGTGAGAAT  180
 41  TyrAspCysThrTrpAsnThrThrThrGlnThrTrpAlaCysSerAsnValSerGluAsn  60

181  GGCTGGCTGAAGGCAGTGCAGGCCCTCATGGTGCTGTCTCTCATCCTCTGCTGCCTGTCC  240
 61  GlyTrpLeuLysAlaValGlnAlaLeuMetValLeuSerLeuIleLeuCysCysLeuSer  80

241  TTCATCCTCTTCATGTTCCAACTCTACACCATGCGGCGCGGAGGGCTCTTCTACGCTACC  300
 81  PheIleLeuPheMetPheGlnLeuTyrThrMetArgArgGlyGlyLeuPheTyrAlaThr  100

301  GGCCTCTGCCAGCTTTGCACCAGTGCAGCTGTGTTCTCCGGGGCACTCATCTATGCCATC  360
101  GlyLeuCysGlnLeuCysThrSerAlaAlaValPheSerGlyAlaLeuIleTyrAlaIle  120

361  CACACCGAGGAGATCCTGGCCAAGCACCCGAGTGGGGGCAGCTTCGGTTACTGCTTCGCC  420
121  HisThrGluGluIleLeuAlaLysHisProSerGlyGlySerPheGlyTyrCysPheAla  140

421  CTGGCCTGGGTGGCTTTTCCACTCGCTCTGGTCAGCGGCATTGTCTACATCCACCTGCGG  480
141  LeuAlaTrpValAlaPheProLeuAlaLeuValSerGlyIleValTyrIleHisLeuArg  160

481  AAACGTGAATGA  492
161  LysArgGlu     163
```

TABLE 5

Alignment of protein sequences of human AVE02, mouse AVE02, human PMP22, and mouse PMP22. Human AVE02 is SEQ ID NO: 2, mouse AVE02 is SEQ ID NO: 4, human PMP22 is SEQ ID NO: 5, and mouse PMP22 is SEQ ID NO: 6. Presumptive membrane spanning segments are underlined. 1 marks a mutation position correlated with CMT; 2 marks a mutation position correlated with mouse trembler; 3 marks a mutation position correlated with both CMT and mouse trembler; and 4 marks a mutation position correlated with CMT and Dejerine-Sottas condition.

```
hAVE02   MSLLLLVVSALHILILILLFVATLDKSWWTLPGKESLNLWYDCTWNNDTKTWACSNVSEN
mAVE02   MSLLLLVVSALHILILVLLFVATLDKSWWTLPDKESLNLWYDCTWNTTTQTWACSNVSEN
hPMP22   MLLLLLSIIVLHVAVLVLLFVSTI-VSQWIVGNGHATDLWQNCSTSSSGNVHHCFSSSPN
mPMP22   MLLLLLGILFLHIAVLVLLFVSTI-VSQWLVGNGHTTDLWQNCTTSALGAVQHCYSSSVS
                      3

hAVE02   GWLKAVQVLMVLSLILCCLSFILFMFQLYTMRRGGLFYATGLCQLCTSVAVFTGALIYAI
mAVE02   GWLKAVQALMVLSLILCCLSFILFMFQLYTMRRGGLFYATGLCQLCTSAAVFSGALIYAI
hPMP22   EWLQSVQATMILSIIFSILSLFLFFCQLFTLTKGGRFYITGIFQILAGLCVMSAAAIYTV
mPMP22   EWLQSVQATMILSVIFSVLALFLFFCQLFTLTKGGRFYITGFFQILAGLCVMSAAAIYTV
                 4 4     1                                       1

hAVE02   HAEEILEKHPRGGSFGYCFALAWVAFPLALVSGIIYIHLRKRE   163
mAVE02   HTEEILAKHPSGGSFGYCFALAWVAFPLALVSGIVYIHLRKRE   163
hPMP22   RHPEWHLN--SDYSYGFAYILAWVAFPLALLSGVIYVILRKRE   160
mPMP22   RHSEWHVN--TDYSYGFAYILAWVAFPLALLSGIIYVILRKRE   160
                                    2
```

The purified protein or defined peptides are useful for generating antibodies by standard methods, as described above. Synthetic peptides or purified protein can be presented to an immune system to generate a specific binding composition, e.g., monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press.

For example, the specific binding composition could be used for screening of an expression library made from a cell line which expresses an AVE02 protein. The screening can be standard staining of surface expressed protein, or by panning. Screening of intracellular expression can also be performed by various staining or immunofluorescence procedures. The binding compositions could be used to affinity purify or sort out cells expressing the protein.

This invention contemplates use of isolated DNA or fragments to encode a biologically active AVE02 protein or polypeptide. In addition, this invention covers isolated or recombinant DNA which encodes a biologically active protein or polypeptide and which is capable of hybridizing under appropriate conditions with the DNA sequences described herein. Said biologically active protein or polypeptide can be an intact antigen, or fragment, and have an amino acid sequence as disclosed in Table 3 or 4. Further, this invention covers the use of isolated or recombinant DNA, or fragments thereof, which encode proteins which are homologous to an AVE02 protein or which were isolated using cDNA encoding an AVE02 protein as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Alternatively, a purified species may be separated from host components from a recombinant expression system.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides. Said fragments may have termini at any location, but especially at boundaries between structural domains.

A DNA which codes for an AVE02 protein will be particularly useful to identify genes, mRNA, and cDNA species which code for related or homologous proteins, as well as DNAs which code for homologous proteins. There are likely homologs in other primates. Various AVE02 proteins should be homologous and are encompassed herein. However, even proteins that have a more distant evolutionary relationship to the antigen can readily be isolated under appropriate conditions using these sequences if they are sufficiently homologous. Primate AVE02 proteins are of particular interest.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987) (ed.) *Teratocarcinomas and Embryonic Stem Cells: A Practical Approach* IRL Press, Oxford; and Rosenberg (1992) *J. Clinical Oncology* 10:180–199; each of which is incorporated herein by reference.

Homologous nucleic acid sequences, when compared, exhibit significant similarity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence derived from Table 3 or 4. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203–213, which is incorporated herein by reference. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349–370, which is hereby incorporated herein by reference.

III. Purified AVE02 Protein

The predicted human AVE02 amino acid sequence is shown in Table 3. The peptide sequences allow preparation of peptides to generate antibodies to recognize such segments, As used herein, AVE02 shall encompass, when used in a protein context, a protein having amino acid sequences shown in Table 3 or 4. Significant fragments of such proteins are thereby provided. Various homologs, e.g., primate, such as human, include highly similar polypeptides which exhibit similar biological function or interacts with AVE02 protein specific binding components. These binding components, e.g., antibodies, typically bind to an AVE02 protein with high affinity, e.g., at least about 100 nM, usually better than about 30 nM, preferably better than about 10 nM, and more preferably at better than about 3 nM.

The term polypeptide, as used herein, includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at Least 20 amino acids, usually at least 22 amino acids, more usually at least 24 amino acids, preferably at least 26 amino acids, more preferably at least 28 amino acids, and, in particularly preferred embodiments, at least about 30 or more amino acids. The specific ends of such a segment will be at any combinations within the protein. Preferably the fragment will encompass intact structural domains, e.g., transmembrane domains 1–31, 66–91, 97–120, and 134–156; extramembrane domains 32–65, 92–96, 121–133, and 157–163.

Substantially pure, in the polypeptide context, typically means that the protein is free from other contaminating proteins, nucleic acids, and other biologicals derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in most preferred embodiments, at least 99% pure. The analysis may be weight or molar percentages, evaluated, e.g., by gel staining, spectrophotometry, or terminus labeling.

A binding composition refers to molecules that bind with specificity to AVE02 protein, e.g., in a ligand-receptor type fashion, an antibody-antigen interaction, or compounds, e.g., proteins which specifically associate with AVE02 protein, e.g., in a natural physiologically relevant protein-protein interaction, either covalent or non-covalent. The molecule may be a polymer, or chemical reagent. No implication as to whether AVE02 protein is either the ligand or the receptor of a ligand-receptor interaction is represented, other than the interaction exhibit similar specificity, e.g., specific affinity. A functional analog may be a protein with structural modifications, or may be a wholly unrelated molecule, e.g., which has a molecular shape which interacts with the appropriate binding determinants. The proteins may serve as agonists or antagonists of a receptor, see, e.g., Goodman, et al. (eds.) (1990) *Goodman & Gilman's: The Pharmacological Bases of Therapeutics* (8th ed.), Pergamon Press.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the antigen.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry*, parts 1–3, W. H. Freeman & Co., San Francisco; each of which is hereby incorporated herein by reference. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30 S, more typically less than about 15 S, usually less than about 10 S, more usually less than about 6 S, and, in particular embodiments, preferably less than about 4 S, and more preferably less than about 3 S.

IV. Making AVE02 Protein; Mimetics

DNA which encodes the AVE02 protein or fragments thereof can be obtained by chemical synthesis, screening cDNA libraries, or by screening genomic libraries prepared from a wide variety of cell lines or tissue samples.

This DNA can be expressed in a wide variety of host cells for the synthesis of a full-length protein or fragments which can in turn, for example, be used to generate polyclonal or monoclonal antibodies; for binding studies; for construction and expression of modified molecules; and for structure/function studies. Each antigen or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encodes an AVE02 protein, or a fragment thereof, typically encoding a biologically active polypeptide. The DNA can be under the control of a viral promoter and can encode a selection marker. This invention further contemplates use of such expression vectors which are capable of expressing eukaryotic cDNA coding for an AVE02 protein in a prokaryotic or eukaryotic host, where the vector is compatible with the host and where the eukaryotic cDNA coding for the antigen is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the antigen or its fragments in various hosts using vectors that do not contain a replication origin that is recognized by the host cell. It is also possible to use vectors that cause integration of an AVE02 gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriquez, et al. (1988) (eds.) *Vectors: A Survey of Molecular Cloning Vectors and Their Uses*, Buttersworth, Boston, Mass., which are incorporated herein by reference.

Transformed cells include cells, preferably mammalian, that have been transformed or transfected with vectors containing an AVE02 gene, typically constructed using recombinant DNA techniques. Transformed host cells usually express the antigen or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, either from the culture or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the AVE02 proteins or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses*, Buttersworth, Boston, Chapter 10, pp. 205–236, which is incorporated herein by reference.

Lower eukaryotes, e.g., yeasts and Dictyostelium, may be transformed with vectors encoding AVE02 proteins. For purposes of this invention, the most common lower eukaryotic host is the baker's yeast, Saccharomyces cerevisiae. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active AVE02 protein. In principle, any higher eukaryotic tissue culture cell line is workable, e.g., insect baculovirus expression systems, whether from an invertebrate or vertebrate source. However, mammalian cells are preferred, in that the processing, both cotranslationally and posttranslationally. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136–1142; pMClneo Poly-A, see Thomas, et al. (1987) *Cell* 51:503–512; and a baculovirus vector such as pAC 373 or pAC 610.

It will often be desired to express an AVE02 protein polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the AVE02 protein gene may be co-transformed with one or more genes encoding mammalian or other glycosylating enzymes. Using this approach, certain mammalian glycosylation patterns will be achievable or approximated in prokaryote or other cells.

The AVE02 protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Now that the AVE02 protein has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York; all of each are incorporated herein by reference. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The AVE02 protein, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149–2156, which is incorporated herein by reference.

The prepared protein and fragments thereof can be isolated and purified from the reaction mixture by means of peptide separation, for example, by extraction, precipitation, electrophoresis and various forms of chromatography, and the like. The AVE02 proteins of this invention can be obtained in varying degrees of purity depending upon its desired use. Purification can be accomplished by use of the protein purification techniques disclosed herein or by the use of the antibodies herein described in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the protein, or lysates or supernatants of cells producing the AVE02 protein as a result of DNA techniques, see below.

V. Physical Variants

This invention also encompasses proteins or peptides having substantial amino acid sequence homology with the amino acid sequence of the AVE02 protein. The variants include species and allelic variants.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25–100% homology (if gaps can be introduced), to 50–100% homology (if conservative substitutions are included) with the amino acid sequence of the AVE02 protein. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.; each of which is incorporated herein by reference.

The isolated DNA encoding an AVE02 protein can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, or antigenic activity. These modified sequences can be used to produce mutant antigens or to enhance expression. Enhanced expression may involve gene amplification, increased transcription, increased translation, and other mechanisms. Such mutant AVE02 protein derivatives include predetermined or site-specific mutations of the respective protein or its fragments. "Mutant AVE02 protein" encompasses a polypeptide otherwise falling within the homology definition of the human AVE02 protein as set forth above, but having an amino acid sequence which differs from that of AVE02 protein as found in nature, whether by way of deletion, substitution, or insertion. In particular, "site specific mutant AVE02 protein" generally includes proteins having significant homology with a protein having sequences of Table 3, and as sharing various biological activities, e.g., antigenic or immunogenic, with those sequences, and in preferred embodiments contain most of the disclosed sequences. Similar concepts apply to different AVE02 proteins, particularly those found in various mammals, e.g., primates, including human. As stated before, it is emphasized that descriptions are generally meant to encompass all AVE02 proteins, not limited to the specific embodiment discussed.

Although site specific mutation sites are predetermined, mutants need not be site specific. AVE02 protein mutagenesis can be conducted by making amino acid insertions or deletions. Substitutions, deletions, insertions, or any combinations may be generated to arrive at a final construct. Insertions include amino- or carboxy- terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with an AVE02 polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, antigen-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992, each of which is incorporated herein by reference. Thus, new chimeric polypeptides exhibiting new combinations of specificities will result from the functional linkage of biologically relevant domains and other functional domains.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

VI. Functional Variants

The blocking of physiological response to AVE02 proteins may result from the inhibition of binding of the antigen to its natural binding partner, e.g., through competitive inhibition. Thus, in vitro assays of the present invention will often use isolated protein, membranes from cells expressing a recombinant membrane associated AVE02 protein, soluble fragments comprising binding segments, or fragments attached to solid phase substrates. These assays will also allow for the diagnostic determination of the effects of either binding segment mutations and modifications, or protein mutations and modifications, e.g., analogs.

This invention also contemplates the use of competitive drug screening assays, e.g., where neutralizing antibodies to antigen or binding partner fragments compete with a test compound for binding to the protein. In this manner, the antibodies can be used to detect the presence of any polypeptide which shares one or more antigenic binding sites of the protein and can also be used to occupy binding sites on the protein that might otherwise interact with a binding partner.

Additionally, neutralizing antibodies against the AVE02 protein and soluble fragments of the antigen which contain a high affinity receptor binding site, can be used to inhibit antigen function in tissues, e.g., tissues experiencing abnormal physiology.

"Derivatives" of the AVE02 antigens include amino acid sequence mutants, glycosylation variants, and covalent or aggregate conjugates with other chemical moieties. Covalent derivatives can be prepared by linkage of functionalities to groups which are found in the AVE02 amino acid side chains or at the N- or C- termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the AVE02 protein or fragments thereof with other proteins or polypeptides. These derivatives can be synthesized in recombinant culture such as N- or C-terminal fusions or by the use of agents known in the art for their usefulness in cross-linking proteins through reactive side groups. Preferred antigen derivatization sites with cross-linking agents are at free amino groups, carbohydrate moieties, and cysteine residues.

Fusion polypeptides between the AVE02 proteins and other homologous or heterologous proteins are also provided. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of an antigen, e.g., a receptor-binding segment, so that the presence or location of the fused antigen may be easily determined. See, e.g., Dull, et al., U.S. Pat. No. 4,859,609, which is hereby incorporated herein by reference. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1–3, Cold Spring Harbor Laboratory, which are incorporated herein by reference. Techniques for synthesis of polypeptides are described, for example, in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach*, IRL Press, Oxford; each of which is incorporated herein by reference.

This invention also contemplates the use of derivatives of the AVE02 proteins other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of antigens or other binding proteins. For example, an AVE02 antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-AVE02 protein antibodies or its receptor or other binding partner. The AVE02 antigens can also be labeled with a detectable group, for example radioiodinated by the chloramine T procedure, covalently bound to rare earth chelates, or conjugated to another fluorescent moiety for use in diagnostic assays. Purification of AVE02 protein may be effected by immobilized antibodies or binding partners.

A solubilized AVE02 antigen or fragment of this invention can be used as an immunogen for the production of antisera or antibodies specific for the protein or fragments thereof. The purified antigen can be used to screen monoclonal antibodies or binding fragments prepared by immunization with various forms of impure preparations containing the protein. In particular, the term "antibodies" also encompasses antigen binding fragments of natural antibodies. The purified AVE02 proteins can also be used as a reagent to detect any antibodies generated in response to the presence of elevated levels of the protein or cell fragments containing the antigen, both of which may be diagnostic of an abnormal or specific physiological or disease condition. Additionally, antigen fragments may also serve as immunogens to produce the antibodies of the present invention, as described immediately below. For example, this invention contemplates antibodies raised against amino acid sequences encoded by nucleotide sequences shown in Table 3, or fragments of proteins containing them. In particular, this invention contemplates antibodies having binding affinity to or being raised against specific fragments which are predicted to lie outside of the lipid bilayer.

The invention also provides means to isolate a group of related antigens displaying both distinctness and similarities in structure, expression, and function. Elucidation of many of the physiological effects of the antigens will be greatly accelerated by the isolation and characterization of distinct species variants. In particular, the present invention provides useful probes for identifying additional homologous genetic entities in different species.

The isolated genes will allow transformation of cells lacking expression of a corresponding AVE02 protein, e.g., either species types or cells which lack corresponding antigens and should exhibit negative background activity. Expression of transformed genes will allow isolation of antigenically pure cell lines, with defined or single specie variants. This approach will allow for more sensitive detection and discrimination of the physiological effects of AVE02 proteins. Subcellular fragments, e.g., cytoplasts or membrane fragments, can be isolated and used.

Dissection of the critical structural elements which effect the various physiological or differentiation functions provided by the proteins is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390; each of which is incorporated herein by reference.

In particular, functional domains or segments can be substituted between species variants or related proteins to determine what structural features are important in both binding partner affinity and specificity, as well as signal transduction. An array of different variants will be used to screen for molecules exhibiting combined properties of interaction with different species variants of binding partners.

Antigen internalization may occur under certain circumstances, and interaction between intracellular components and "extracellular" segments of proteins involved in interactions may occur. The specific segments of interaction of AVE02 protein with other intracellular components may be identified by mutagenesis or direct biochemical means, e.g., cross-linking or affinity methods. Structural analysis by crystallographic or other physical methods will also be applicable. Further investigation of the mechanism of biological function will include study of associated components which may be isolatable by affinity methods or by genetic means, e.g., complementation analysis of mutants.

Further study of the expression and control of AVE02 protein will be pursued. The controlling elements associated with the antigens may exhibit differential developmental, tissue specific, or other expression patterns. Upstream or downstream genetic regions, e.g., control elements, are of interest.

Structural studies of the antigen will lead to design of new variants, particularly analogs exhibiting agonist or antagonist properties on binding partners. This can be combined with previously described screening methods to isolate variants exhibiting desired spectra of activities.

Expression in other cell types will often result in glycosylation differences in a particular antigen. Various species variants may exhibit distinct functions based upon structural differences other than amino acid sequence. Differential modifications may be responsible for differential function, and elucidation of the effects are now made possible.

Thus, the present invention provides important reagents related to antigen-binding partner interaction. Although the foregoing description has focused primarily upon the human AVE02 protein, those of skill in the art will immediately recognize that the invention encompasses other closely related antigens, e.g., other primate species or allelic variants, as well as variants and other members of the family.

VII. Antibodies

Antibodies can be raised to the various AVE02 proteins, including species or allelic variants, and fragments thereof, both in their naturally occurring forms and in their recombinant forms. Additionally, antibodies can be raised to AVE02 proteins in either their active forms or in their inactive forms. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective AVE02 proteins, or screened for agonistic or antagonistic activity, e.g., mediated through a binding partner. These monoclonal antibodies will usually bind with at least a KD of about 1 mM, more usually at least about 300 $\mu$M, typically at least about 100 $\mu$M, more typically at least about 30 $\mu$M, preferably at least about 10 $\mu$M, and more preferably at least about 3 $\mu$M or better.

The antibodies, including antigen binding fragments, of this invention can have significant diagnostic or therapeutic value. They can be potent antagonists that bind to a binding partner and inhibit antigen binding or inhibit the ability of an antigen to elicit a biological response. They also can be useful as non-neutralizing antibodies and can be coupled to toxins or radionuclides so that when the antibody binds to the antigen, a cell expressing it, e.g., on its surface, is killed. Further, these antibodies can be conjugated to drugs or other therapeutic agents, either directly or indirectly by means of a linker, and may effect drug targeting.

The antibodies of this invention can also be useful in diagnostic applications. As capture or non-neutralizing antibodies, they can be screened for ability to bind to the antigens without inhibiting binding by a partner. As neutralizing antibodies, they can be useful in competitive binding assays. They will also be useful in detecting or quantifying AVE02 protein or its binding partners.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York, and Williams, et al. (1967) *Methods in Immunology and Immunochemistry*, Vol. 1, Academic Press, New York, each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256: 495–497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567. These patents are incorporated herein by reference.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified AVE02 protein will be released.

The antibodies may also be used to screen expression libraries for particular expression products. Usually the antibodies used in such a procedure will be labeled with a moiety allowing easy detection of presence of antigen by antibody binding.

Antibodies raised against each AVE02 protein will also be useful to raise anti-idiotypic antibodies. These will be useful in detecting or diagnosing various immunological conditions related to expression of the respective antigens.

VIII. Uses

The present invention provides reagents which will find use in diagnostic applications as described elsewhere herein, e.g., in the general description for physiological or developmental abnormalities, or below in the description of kits for diagnosis.

This invention also provides reagents with significant therapeutic value. The AVE02 protein (naturally occurring or recombinant), fragments thereof, and antibodies thereto, along with compounds identified as having binding affinity to AVE02 protein, should be useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by an AVE02 antigen should be a likely target for an agonist or antagonist of the protein.

Other abnormal developmental conditions are known in the cell types shown to possess AVE02 antigen mRNA by Northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, N.Y. These problems may be susceptible to prevention or treatment using compositions provided herein.

Recombinant antibodies which bind to AVE02 can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Screening using AVE02 for binding partners or compounds having binding affinity to AVE02 antigen can be performed, including isolation of associated components. Subsequent biological assays can then be utilized to determine if the compound has intrinsic biological activity and is therefore an agonist or antagonist in that it blocks an activity of the antigen. This invention further contemplates the therapeutic use of antibodies to AVE02 protein as antagonists. This approach should be particularly useful with other AVE02 protein species variants and other members of the family.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

AVE02 protein, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; each of which is hereby incorporated herein by reference. The therapy of this invention may be combined with or used in association with other chemotherapeutic or chemopreventive agents.

Both the naturally occurring and the recombinant form of the AVE02 proteins of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which is incorporated herein by reference and which describes means for testing of binding affinity by a plurality of defined polymers synthesized on a solid substrate. The development of suitable assays can be greatly facilitated by the availability of large amounts of purified, soluble AVE02 protein as provided by this invention.

This invention is particularly useful for screening compounds by using recombinant antigen in any of a variety of drug screening techniques. The advantages of using a recombinant protein in screening for specific ligands include: (a) improved renewable source of the antigen from a specific source; (b) potentially greater number of antigen molecules per cell giving better signal to noise ratio in assays; and (c) species variant specificity (theoretically giving greater biological and disease specificity). The purified protein may be tested in numerous assays, typically in vitro assays, which evaluate biologically relevant responses. See, e.g., Coligan *Current Protocols in Immunology*; Hood, et al. *Immunology* Benjamin/Cummings; Paul (ed.) *Fundamental Immunology*; and *Methods in Enzymology* Academic Press. This will also be useful in screening for a ligand which binds an AVE02, e.g., from an interacting cell.

One method of drug screening utilizes eukaryotic or prokaryotic host cells which are stably transformed with recombinant DNA molecules expressing the AVE02 antigens. Cells may be isolated which express an antigen in isolation from other functionally equivalent antigens. Such cells, either in viable or fixed form, can be used for standard protein-protein binding assays. See also, Parce, et al. (1989) *Science* 246:243–247; and Owicki, et al. (1990) *Proc. Nat'l Acad. Sci. USA* 87:4007–4011, which are incorporated herein by reference and describe sensitive methods to detect cellular responses. Competitive assays are particularly useful, where the cells (source of AVE02 protein) are contacted and incubated with a labeled binding partner or antibody having known binding affinity to the ligand, such as $^{125}I$-antibody, and a test sample whose binding affinity to the binding composition is being measured. The bound and free labeled binding compositions are then separated to assess the degree of antigen binding. The amount of test compound bound is inversely proportional to the amount of labeled receptor binding to the known source. Any one of numerous techniques can be used to separate bound from free antigen to assess the degree of binding. This separation step could typically involve a procedure such as adhesion to filters followed by washing, adhesion to plastic followed by washing, or centrifugation of the cell membranes. Viable cells could also be used to screen for the effects of drugs on AVE02 protein mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as the source of the AVE02 protein. These cells are stably transformed with DNA vectors directing the expression of a membrane associated AVE02 protein, e.g., an engineered membrane bound form. Essentially, the membranes would be prepared from the cells and used in any receptor/ligand type binding assay such as the competitive assay set forth above.

Still another approach is to use solubilized, unpurified or solubilized, purified AVE02 protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to AVE02 and is described in detail in Geysen, European Patent Application 84/03564, published on Sep. 13, 1984, which is incorporated herein by reference. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified AVE02 binding composition, and washed. The next step involves detecting bound binding composition.

Rational drug design may also be based upon structural studies of the molecular shapes of the AVE02 protein and other effectors or analogs. Effectors may be other proteins which mediate other functions in response to antigen binding, or other proteins which normally interact with the antigen, e.g., AVE02 ligand. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York, which is hereby incorporated herein by reference.

Purified AVE02 protein can be coated directly onto plates for use in the aforementioned drug screening techniques. However, non-neutralizing antibodies to these ligands can be used as capture antibodies to immobilize the respective ligand on the solid phase.

IX. Kits

This invention also contemplates use of AVE02 proteins, fragments thereof, peptides, and their fusion products in a variety of diagnostic kits and methods for detecting the presence of a binding composition. Typically the kit will have a compartment containing either a defined AVE02 peptide or gene segment or a reagent which recognizes one or the other, e.g., antigen fragments or antibodies.

A kit for determining the binding affinity of a test compound to an AVE02 protein would typically comprise a test compound; a labeled compound, for example an antibody having known binding affinity for the antigen; a source of AVE02 protein (naturally occurring or recombinant); and a means for separating bound from free labeled compound, such as a solid phase for immobilizing the antigen. Once compounds are screened, those having suitable binding affinity to the antigen can be evaluated in suitable biological assays, as are well known in the art, to determine whether they exhibit similar biological activities to the natural antigen. The availability of recombinant AVE02 protein polypeptides also provide well defined standards for calibrating such assays.

A preferred kit for determining the concentration of, for example, an AVE02 protein in a sample would typically comprise a labeled compound, e.g., antibody, having known binding affinity for the antigen, a source of antigen (naturally occurring or recombinant) and a means for separating the bound from free labeled compound, for example, a solid phase for immobilizing the AVE02 protein. Compartments containing reagents, and instructions, will normally be provided.

One method for determining the concentration of AVE02 protein in a sample would typically comprise the steps of: (1) preparing membranes from a sample comprised of a membrane bound AVE02 protein source; (2) washing the membranes and suspending them in a buffer; (3) solubilizing the antigen by incubating the membranes in a culture medium to which a suitable detergent has been added; (4) adjusting the detergent concentration of the solubilized antigen; (5) contacting and incubating said dilution with radiolabeled antibody to form complexes; (6) recovering the complexes such as by filtration through polyethyleneimine treated filters; and (7) measuring the radioactivity of the recovered complexes.

Antibodies, including antigen binding fragments, specific for the AVE02 protein or fragments are useful in diagnostic applications to detect the presence of elevated levels of AVE02 protein and/or its fragments. Such diagnostic assays can employ lysates, live cells, fixed cells, immunofluorescence, cell cultures, body fluids, and further can involve the detection of antigens related to the protein in serum, or the like. Diagnostic assays may be homogeneous (without a separation step between free reagent and protein-protein complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to an AVE02 protein or to a particular fragment thereof. Similar assays have also been extensively discussed in the literature. See, e.g., Harlow and Lane (1988) *Antibodies: A Laboratory Manual*, CSH.

Anti-idiotypic antibodies may have similar use to diagnose presence of antibodies against an AVE02 protein, as such may be diagnostic of various abnormal states. For example, overproduction of AVE02 protein may result in production of various immunological reactions which may be diagnostic of abnormal physiological states, particularly in proliferative cell conditions such as cancer or abnormal differentiation.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled AVE02 protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the antigen, test compound, AVE02 protein, or antibodies thereto can be labeled either directly or indirectly. Possibilities for direct labeling include label groups: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free antigen, or alternatively the bound from the free test compound. The AVE02 protein can be immobilized on various matrixes followed by washing. Suitable matrixes include plastic such as an ELISA plate, filters, and beads. Methods of immobilizing the AVE02 protein to a matrix include, without limitation, direct adhesion to plastic, use of a capture antibody, chemical coupling, and biotin-avidin. The last step in this approach involves the precipitation of protein-protein complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678, each of which is incorporated herein by reference.

The methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an AVE02 protein. These sequences can be used as probes for detecting levels of antigen message in samples from patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}P$. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

x. Methods for Isolating AVE02 Specific Binding Partners

The AVE02 protein should interact with a ligand based, e.g., upon its similarity in structure and function to other cell markers exhibiting developmental and cell type specificity of expression. One likely candidate is a homotypic interaction, e.g., AVE02 with another molecule of AVE02. Methods to isolate a ligand are made available by the ability to make purified AVE02 for screening programs. Soluble or other constructs using the AVE02 sequences provided herein will allow for screening or isolation of AVE02 specific ligands or binding compositions.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual, (*2d ed.), vols 1–3, CSH Press, NY; Ausubel, et al., *Biology*, Greene Publishing Associates, Brooklyn, N.Y.; or Ausubel, et al. (1987 and Supplements) *Current Protocols in Molecular Biology, Greene/Wiley, New York; Innis, et al. (eds.) (*1990) *PCR Protocols: A Guide to Methods and Applications* Academic Press, N.Y.; all of which are each incorporated herein by reference. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; and manufacturer's literature on use of protein purification products, e.g., Pharmacia, Piscataway, N.J., or Bio-Rad, Richmond, Calif.; which are incorporated herein by reference. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexpress: The High Level Expression & Protein Purification System* QUIAGEN, Inc., Chatsworth, Calif.: which are incorporated herein by reference.

FACS analyses are described in Melamed, et al. (1990) *Flow Cytometry and Sorting* Wiley-Liss, Inc., New York, N.Y; Shapiro (1988) *Practical Flow Cytometry Liss, New York, N.Y; and Robinson, et al. (*1993) *Handbook of Flow Cytometry Methods* Wiley-Liss, New York, N.Y.

II. Preparation of Antibodies Specific for AVE02.

Balb/c mice are immunized with cultured peripheral blood T cells. Splenocytes are fused with the Sp2/0 fusion partner and hybridomas are selected in growth medium containing azaserine by standard procedures.

In another method, synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. In appropriate situations, the binding reagent is either labeled as described above, e.g., fluorescence or otherwise, or immobilized to a substrate for panning methods. Nucleic acids may also be introduced into cells in an animal to produce the antigen, which serves to elicit an immune response. See, e.g., Wang, et al. (1993) *Proc. Natl. Acad. Sci.* 90:4156–4160; Barry, et al. (1994) BioTechniaues 16:616–619; and Xiang, et al. (1995) *Immunity* 2:129–135.

III. Distribution of AVE02 Antigen.

AVE02 antigen distribution may be determined, e.g., by western blots, screening for message, FACS analysis, or other means. Total RNA from various cell lines, populations of cells, and tissues were isolated by standard methods. The RNA samples were then fractionated on denaturing agarose gels, transferred to a solid support, e.g., nitrocellulose, and hybridized with an AVE02 cDNA probe, as provided herein. Washed filters were subsequently exposed to X-ray film, or hybridization can be detected by other methods, e.g., histochemical type staining. The results of these are: U937 (resting monocyte cell line) +++; C− (elutriated monocytes, activated with LPS for 1 h) +++; C+ (elutriated monocytes, activated with LPS for 6 h) +++; M1 (elutriated monocytes activated with LPS, IFN-γ, and anti-IL-10 for 1, 2, 6, 12, 24 h (pooled)) +++; M6 (elutriated monocytes activated with LPS, IFN-γ, and anti-IL-10 for 1, 2, 6, 12, 24 h (pooled)) ++; 70% DC (resting 70% CD1a+ dendritic cells, proliferated in TNF-α and GM-CSF) +; D1 (dendritic cells stimulated 1 h in PMA and ionomycin) +; D6 (dendritic cells stimulated 6 h in PMA and ionomycin) +; D5 DC (resting dendritic cells cultured 5 d in GM-CSF and IL-4) ++; DC (dendritic cells cultured in GM-CSF and IL-4, LPS activated) ++; resting PBMC ++; PBMC activated with anti-CD3 and PMA for 1 h +; resting pooled NK cells +; activated NK pool (with PMA) +; HY06 (resting Th1 clone) +++; HY06 (activated with anti-CD28 and anti-CD3) ++; HY06α (activated with anti-peptide, anergic clone) +++; HY935 (resting Th2 clone) +; HY935 (activated with anti-CD28 and anti-CD3) +; BC pool of EBV transformed lines +; resting splenocytes ++; splenocytes (activated using B cell stimulating conditions, with anti-CD40 and IL-4) ++; fetal kidney (+); fetal lung (++); fetal liver (+); fetal heart +; fetal brain −; fetal gall bladder +; fetal small intestine +; fetal adipose ++; fetal ovary +; fetal uterus ++; adult placenta +; fetal testis ++; and fetal spleen ++.

With human clone: rat normal joint +; rat arthritic joint +; mus (Nippo-infected lung) (+); RAW 264.7 (mouse macrophage from bone marrow); rat hypothalamus −.

Screening may also be performed using immunochemical staining, using either indirect or direct labeling, as described above.

Further testing of populations of progenitor B cells or progenitor T cells can be performed. Other tissue types, at defined developmental stages, and pathology samples will be screened to determine what pathological states or stages may be advantageously correlated with the marker.

IV Biochemical Characterization of the AVE02 Protein.

A recombinant AVE02 construct is prepared, e.g., as a fusion product with a useful affinity reagent, e.g., FLAG peptide. This peptide segment may be useful for purifying the expression product of the construct. See, e.g., Crowe, et al. (1992) *QIAexpress: The High Level Expression & Protein Purification System* QUIAGEN, Inc. Chatsworth, Calif.; and Hopp, et al. (1988) *Bio/Technology* 6:1204–1210. The sequence allows for efficient affinity purification of the soluble product. Appropriate secretion or processing sites may also be engineered into the construct by standard methods. Purification is achieved, e.g., by use of affinity purification such as antibodies against the antigen, or by standard protein purification methods. Typically, the affinity reagents or purification procedures can be performed using monoclonal antibodies.

Affinity reagents can also be produced which allow isolation from natural sources. An ELISA may be used to detect the protein to assist in developing a fractionation protocol, and the purified material should be subject to such characterization as molecular weight, glycosylation, post-translational modifications, amino acid analysis, behavior on various chromatographic analyses such as ion exchange, hydrophobic, size exclusion, HPLC, and others. The product should also be subject to various physical analyses, such as circular dichroism, NMR, mass spectroscopy, etc., before or after such processing as protease or other fragmentation.

V. Purification of AVE02 Protein

The AVE02 protein is isolated by a combination of affinity chromatography using, e.g., the AVE02 specific binding compositions, e.g., antibody, as a specific binding reagent in combination with protein purification techniques allowing separation from other proteins and contaminants. Since the protein appears to be intimately associated with lipid, various detergents may be useful for gentle solubilization of the molecule, e.g., those detergents used successfully in solubilizing 7 transmembrane proteins. Similar techniques using human cell assays and human cell sources are applied to isolate a native human antigen.

VI. Isolation of a cDNA Clone Encoding AVE02 Protein.

Generation of Monocyte Cells

Healthy donors were subjected to a leukophoresis. Percoll gradients were used to isolate mononuclear cells which were then subject to centrifugal elutriation. See, Figdor, et al. (1982) *Blood* 60:46–53; and Plas, et al. (1988) Expt'l. Hematol. 16:355–359. This highly enriched monocyte fraction is cultured for 5–7 days in the presence of GM-CSF (800 U/ml) and IL-4 (500 U/ml), as described in Romani, et al (1994) *J. Exp. Med.* 180:83–93; and Sallusto, et al (1994) *J. Exp. Med.* 179:1109–1118. Dendritic cells are then either harvested and frozen, or stimulated with IL-1α (75 LAF U/ml) and TNF-α (15 ng/ml); LPS (2 μg/ml); or 50% monocyte supernatant for 4 and 20 hours. These stimulated cells are then harvested at appropriate times.

Monocyte supernatant is obtained by adhering mononuclear cells to plastic for 2 hours. Non-adherent cells are removed by washing. The remaining adherent cells are cultured for 24 hours in Iscoves media containing 5% Fetal Calf Serum.

Alternatively, CD34+ monocytes may be isolated and cultured. Cells are cultured in the presence of Stem Cell Factor (SCF), GM-CSF, and TNF-α in endotoxin free RPMI 1640 medium (GIBCO, Grand Island, N.Y.) supplemented with 10% (v/v) heat-inactivated fetal bovine serum (FBS; Flow Laboratories, Irvine, Calif.), 10 mM HEPES, 2 mM L-glutamine, $5\times10^{-5}$ M 2-mercaptoethanol, and penicillin (100 μg/ml). This is referred to as complete medium.

CD34+ cells are seeded for expansion in 25 to 75 $cm^2$ flasks (Corning, N.Y.) at $2\times10^4$ cells/ml. Good growth conditions are maintained, e.g., by splitting the cultures at day 5 and 10 with medium containing fresh GM-CSF and TNF-α (cell concentration: $1–3\times10^5$ cells/ml). Cells are routinely collected after 12 days of culture, eventually adherent cells are recovered using a 5 mM EDTA solution.

Cells are activated by resuspension in complete medium at $5\times10^6$ cells/ml and activated for the appropriate time (e.g., 1 or 6 h) with 1 μg/ml phorbol 12-myristate 13-acetate (PMA, Sigma) and 100 ng/ml ionomycin (Calbiochem, La Jolla, Calif.).

RNA Isolation and Library Construction

Total RNA can be isolated using the guanidine thiocyanate/CsCl gradient procedure as described by Chirgwin, et al. (1978) *Biochem.* 18:5294–5299. Poly(A)+ RNA is isolated using, e.g., the OLIGOTEX mRNA isolation kit (QIAGEN). Double stranded cDNA was generated using, e.g., the SUPERSCRIPT plasmid system (Gibco BRL, Gaithersburg, Md.) for cDNA synthesis and plasmid cloning. Standard procedures for making a cDNA library are available.

IV. Sequencing

DNA isolated from randomly picked clones were subjected to nucleotide sequence analysis using standard techniques. A Taq DiDeoxy Terminator cycle sequencing kit (Applied Biosystems, Foster City, Calif.) can be used. The labeled DNA fragments can be separated using a DNA sequencing gel of an appropriate automated sequencer. Alternatively, the isolated clone is sequenced as described, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York. Chemical sequencing methods are also available, e.g., using Maxam and Gilbert sequencing techniques.

Construction of cDNA Libraries

Pooled poly (A)+ RNA from monocytes (treated with LPS, IFN-γ, and anti-IL-10 for 1, 2, 6, 12, or 24 h) was used to synthesize first strand cDNA. Double-stranded cDNA was synthesized, ligated with adapters, digested, and ligated into vector. See, e.g., Takebe, et al. *Mol. Cell Biol.* 8:466–472. Clones were further characterized by DNA sequencing.

In another method, oligonucleotides are used to screen a library. In combination with polymerase chain reaction (PCR) techniques, synthetic oligonucleotides in appropriate orientations are used as primers to select correct clones from a library.

The AVE02 is used for screening of a library made from a cell line which expresses an AVE02 binding protein, e.g., a ligand. Standard staining techniques are used to detect or sort intracellular or surface expressed ligand, or surface expressing transformed cells are screened by panning. Screening of intracellular expression is performed by various staining or immunofluorescence procedures. See also McMahan, et al. (1991) *EMBO J.* 10:2821–2832.

For example, on day 0, precoat 2-chamber permanox slides with 1 ml per chamber of fibronectin, 10 ng/ml in PBS, for 30 min at room temperature. Rinse once with PBS. Then plate COS cells at 2–3×$10^5$ cells per chamber in 1.5 ml of growth media. Incubate overnight at 37° C.

On day 1 for each sample, prepare 0.5 ml of a solution of 66 $\mu$g/ml DEAE-dextran, 66 $\mu$M chloroquine, and 4 $\mu$g DNA in serum free DME. For each set, a positive control is prepared, e.g., of huIL-10-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 $\mu$/ml of 1M $NaN_3$ for 20 min. Cells are then washed with HBSS/saponin 1×. Soluble antibody is added to cells and incubate for 30 min. Wash cells twice with HBSS/saponin. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85–90° C.

Alternatively, the AVE02 proteins are used to affinity purify or sort out cells expressing the antigen. See, e.g., Sambrook, et al. or Ausubel et al, which are incorporated herein by reference. The antigen is typically expressed on the cell surface.

Hybridization approaches may also be utilized to find closely related variants of the antigen based upon nucleic acid hybridization.

All references cited herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

| SEQUENCE SUBMISSION |
|---|
| SEQ ID NO: 1 is a human AVE02 cDNA sequence. |
| SEQ ID NO: 2 is a human AVE02 polypeptide sequence. |
| SEQ ID NO: 3 is a mouse AVE02 cDNA sequence. |
| SEQ ID NO: 4 is a mouse AVE02 polypeptide sequence. |
| SEQ ID NO: 5 is a human PMP22 polypeptide sequence. |
| SEQ ID NO: 6 is a mouse PMP22 polypeptide sequence. |

What is claimed is:

1. As isolated compound comprising the antigen binding portion from an antibody which specifically binds to residues 32–133 of either SEQ ID NO: 2 or 4.

2. The binding compound of claim 1, which:

a) is substantially pure of ribosomal or polymerase proteins;

b) is substantially pure of nucleic acids;

c) binds to a denatured AVE02 polypeptide of residues 32–133 of either SEQ ID NO: 2 or 4;

d) binds to said mammalian AVE02 of residues 32–133 of either SEQ ID NO: 2 or 4 with a kD of at least 30 $\mu$M;

e) is conjugated to another chemical moiety selected from the group consisting of radionuclides, enzymes, substrates, cofactors, inhibitors, fluorescent moieties, chemiluminescent moieties, or magnetic particles;

f) is a monoclonal antibody;

g) is from a mammalian hybridoma;

h) is attached to a solid substrate;

i) is detectably labeled;

j) is in a sterile composition; or k) is in a buffered aqueous solution.

3. A kit comprising said binding compound of claim 2, and:

a) instructions; or b) a compartment with a reagent used in detecting said binding conpound.

4. A cell which:

a) produces the antibody from which the binding compound of claim 1 is obtained; or b) is labeled with the binding compound of claim 1.

5. A binding compound comprising the antigen binding portion from an antibody which specifically binds to:

a) a polypeptide comprising:
   1) residues 32–65 of SEQ ID NO:2;
   2) residues 66–91 of SEQ ID NO:2;
   3) residues 92–96 of SEQ ID NO:2;
   4) residues 97–120 of SEQ ID NO:2; or
   5) residues 121–133 of SEQ ID NO:2; or b) a polypeptide comprising:
   1) residues 32–65 of SEQ ID NO:4;
   2) residues 66–91 of SEQ ID NO:4;
   3) residues 92–96 of SEQ ID NO:4;
   4) residues 97–120 of SEQ ID NO:4; or
   5) residues 121–133 of SEQ ID NO:4.

6. The binding compound of claim 5, which specifically binds to said polypeptide comprising:

a) residues 32–65 of SEQ ID NO: 2;

b) residues 92–95 of SEQ ID NO: 2;

c) residues 121–133 of SEQ ID NO: 2; or d) residues 32–133 of SEQ ID NO: 2.

7. The binding compound of claim 6, which:

a) is substantially pure of ribosomal or polymerase proteins;

b) is substantially pure of nucleic acids;

c) binds to denatured polypeptide;

d) binds to said polypeptide with a kD of at least 30 $\mu$M;

e) is conjugated to another chemical moiety selected from the group consisting of radionuclides, enzymes, substrates, cofactors, inhibitors, fluorescent moieties, chemiluminescent moieties, or magnetic particles;

f) is a polyclonal antiserum;

g) is a monoclonal antibody;

h) is from a mammalian hybridoma;

i) is attached to a solid substrate;

j) is detectably labeled;

k) is in a sterile composition; or l) is in a buffered aqueous solution.

8. The binding compound of claim 5, which specifically binds to said polypeptide comprising:

a) residues 32–65 of SEQ ID NO: 4;

b) residues 92–95 of SEQ ID NO: 4;

c) residues 121–133 of SEQ ID NO: 4; or d) residues 32–133 of SEQ ID NO: 4.

9. The binding compound of claim 8, which:

a) is substantially pure of ribosomal or polymerase proteins;

b) is substantially pure of nucleic acids;

c) binds to denatured polypeptide;

d) binds to said polypeptide with a kD of at least 30 $\mu$M;

e) is conjugated to another chemical moiety selected from the group consisting of radionuclides, enzymes, substrates, cofactors, inhibitors, fluorescent moieties, chemiluminescent moieties, or magnetic particles;

f) is a polyclonal antiserum;

g) is a monoclonal antibody;

h) is from a mammalian hybridoma;

i) is attached to a solid substrate;

j) is detectably labeled;

k) is in a sterile composition; or l) is in a buffered aqueous solution.

10. A kit comprising said binding compound of claim 6, and:

a) instructions; or b) a compartment with a reagent used in detecting said binding compound.

11. A kit comprising said binding compound of claim 8, and:

a) instructions; or b) a compartment with a reagent used in detecting said binding compound.

12. A cell which:

a) produces the antibody from which the binding compound of claim 6 is obtained; or b) is labeled with the binding compound of claim 6.

13. A cell which:

a) produces the antibody from which the binding compound of claim 8 is obtained; or b) is labeled with the binding compound of claim 8.

14. An isolated binding compound comprising the antigen binding portion from an antibody which binds to a mammalian AVE02 polypeptide which is encoded by the complete complement of a nucleic acid which hybridizes to nucleotides 96–399 of either SEQ ID NO: 1 or 3 at 65° C. and 150 mM salt and which binds to an epitope found in the region defined by amino acids 32–133 of SEQ ID NO:2 or SEQ ID NO:4.

15. The binding compound of claim 14, which:

a) is substantially pure of ribosomal or polymerase proteins;

b) is substantially pure of nucleic acids;

c) binds to a denatured AVE02;

d) binds to said mammalian AVE02 with a kD of at least 30 $\mu$M;

e) is conjugated to another chemical moiety selected from the group consisting of radionuclides, enzymes, substrates, cofactors, inhibitors, fluorescent moieties, chemiluminescent moieties, or magnetic particles;

f) is a polyclonal antiserum;

g) is a monoclonal antibody;

h) is from a mammalian hybridoma;

i) is attached to a solid substrate;

j) is detectably labeled;

k) is in a sterile composition; or l) is in a buffered aqueous solution.

16. A binding compound comprising the antigen binding portion from an antibody which binds to a protein encoded by nucleotides 96–399 of SEQ ID NO:1.

17. The binding compound of claim 16, which:

a) is substantially pure of ribosomal or polymerase proteins;

b) is substantially pure of nucleic acids;

c) binds to a denatured AVE02;

d) binds to said mammalian AVE02 with a kD of at least 30 $\mu$M;

e) is conjugated to another chemical moiety selected from the group consisting of radionuclides, enzymes, substrates, cofactors, inhibitors, fluorescent moieties, chemiluminescent moieties, or magnetic particles;

f) is a monoclonal antibody;

g) is from a mammalian hybridoma;

h) is attached to a solid substrate;

i) is detectably labeled;

j) is in a sterile composition; or k) is in a buffered aqueous solution.

18. The binding compound of claim 1, wherein said residues are primate AVE02 polypeptide.

19. The binding compound of claim 1, wherein said residues are rodent AVE02 polypeptide.

20. A kit comprising said binding compound of claim 1 and:

a) instructions; or b) a compartment with a reagent used in detecting said binding compound.

21. A kit comprising said binding compound of claim 14, and:

a) instructions; or b) a compartment with a reagent used in detecting said binding compound.

22. A cell which:

a) produces the antibody from which the binding compound of claim 14 is obtained; or b) is labeled with the binding compound of claim 14.

* * * * *

SEQUENCE LISTING

```
(1) GENERAL INFORMATION:

   (iii) NUMBER OF SEQUENCES: 6


(2) INFORMATION FOR SEQ ID NO:1:

     (i) SEQUENCE CHARACTERISTICS:
          (A) LENGTH: 492 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 1..492

    (xi) SEQUENCE DESCRIPTION: SEQ ID NO:1:

ATG TCA CTC CTC TTG CTG GTG GTC TCA GCC CTT CAC ATC CTC ATT CTT        48
Met Ser Leu Leu Leu Leu Val Val Ser Ala Leu His Ile Leu Ile Leu
  1               5                  10                  15

ATA CTG CTT TTC GTG GCC ACT TTG GAC AAG TCC TGG TGG ACT CTC CCT        96
Ile Leu Leu Phe Val Ala Thr Leu Asp Lys Ser Trp Trp Thr Leu Pro
             20                  25                  30

GGG AAA GAG TCC CTG AAT CTC TGG TAC GAC TGC ACG TGG AAC AAC GAC       144
Gly Lys Glu Ser Leu Asn Leu Trp Tyr Asp Cys Thr Trp Asn Asn Asp
         35                  40                  45

ACC AAA ACA TGG GCC TGC AGT AAT GTC AGC GAG AAT GGC TGG CTG AAG       192
```

-continued

```
Thr Lys Thr Trp Ala Cys Ser Asn Val Ser Glu Asn Gly Trp Leu Lys
     50                  55                  60

GCG GTG CAG GTC CTC ATG GTG CTC TCC CTC ATT CTC TGC TGT CTC TCC       240
Ala Val Gln Val Leu Met Val Leu Ser Leu Ile Leu Cys Cys Leu Ser
 65                  70                  75                  80

TTC ATC CTG TTC ATG TTC CAG CTC TAC ACC ATG CGA CGA GGA GGT CTC       288
Phe Ile Leu Phe Met Phe Gln Leu Tyr Thr Met Arg Arg Gly Gly Leu
                 85                  90                  95

TTC TAT GCC ACC GGC CTC TGC CAG CTT TGC ACC AGC GTG GCG GTG TTT       336
Phe Tyr Ala Thr Gly Leu Cys Gln Leu Cys Thr Ser Val Ala Val Phe
            100                 105                 110

ACT GGC GCC TTG ATC TAT GCC ATT CAC GCC GAG GAG ATC CTG GAG AAG       384
Thr Gly Ala Leu Ile Tyr Ala Ile His Ala Glu Glu Ile Leu Glu Lys
        115                 120                 125

CAC CCG CGA GGG GGC AGC TTC GGA TAC TGC TTC GCC CTG GCC TGG GTG       432
His Pro Arg Gly Gly Ser Phe Gly Tyr Cys Phe Ala Leu Ala Trp Val
    130                 135                 140

GCC TTC CCC CTC GCC CTG GTC AGC GGC ATC ATC TAC ATC CAC CTA CGG       480
Ala Phe Pro Leu Ala Leu Val Ser Gly Ile Ile Tyr Ile His Leu Arg
145                 150                 155                 160

AAG CGG GAG TGA                                                       492
Lys Arg Glu  *
```

(2) INFORMATION FOR SEQ ID NO:2:

(i) SEQUENCE CHARACTERISTICS:
(A) LENGTH: 163 amino acids
(B) TYPE: amino acid
(D) TOPOLOGY: linear (ii) MOLECULE TYPE: protein (xi) SEQUENCE DESCRIPTION: SEQ ID NO:2:

```
Met Ser Leu Leu Leu Leu Val Val Ser Ala Leu His Ile Leu Ile Leu
  1               5                  10                  15

Ile Leu Leu Phe Val Ala Thr Leu Asp Lys Ser Trp Trp Thr Leu Pro
             20                  25                  30

Gly Lys Glu Ser Leu Asn Leu Trp Tyr Asp Cys Thr Trp Asn Asn Asp
         35                  40                  45

Thr Lys Thr Trp Ala Cys Ser Asn Val Ser Glu Asn Gly Trp Leu Lys
     50                  55                  60

Ala Val Gln Val Leu Met Val Leu Ser Leu Ile Leu Cys Cys Leu Ser
 65                  70                  75                  80

Phe Ile Leu Phe Met Phe Gln Leu Tyr Thr Met Arg Arg Gly Gly Leu
                 85                  90                  95

Phe Tyr Ala Thr Gly Leu Cys Gln Leu Cys Thr Ser Val Ala Val Phe
            100                 105                 110

Thr Gly Ala Leu Ile Tyr Ala Ile His Ala Glu Glu Ile Leu Glu Lys
        115                 120                 125

His Pro Arg Gly Gly Ser Phe Gly Tyr Cys Phe Ala Leu Ala Trp Val
    130                 135                 140

Ala Phe Pro Leu Ala Leu Val Ser Gly Ile Ile Tyr Ile His Leu Arg
145                 150                 155                 160

Lys Arg Glu
```

(2) INFORMATION FOR SEQ ID NO:3:

(i) SEQUENCE CHARACTERISTICS:
(A) LENGTH: 492 base pairs

-continued (B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..492

(xi) SEQUENCE DESCRIPTION: SEQ ID NO:3:

```
ATG TCA CTC CTC CTG TTG GTG GTC TCT GCC CTC CAC ATC CTC ATT CTT        48
Met Ser Leu Leu Leu Leu Val Val Ser Ala Leu His Ile Leu Ile Leu
  1               5                  10                  15

GTC TTG CTT TTT GTG GCC ACT TTG GAC AAG TCC TGG TGG ACT CTC CCA        96
Val Leu Leu Phe Val Ala Thr Leu Asp Lys Ser Trp Trp Thr Leu Pro
             20                  25                  30

GAC AAA GAG TCC CTG AAC CTG TGG TAT GAC TGC ACG TGG AAC ACC ACC       144
Asp Lys Glu Ser Leu Asn Leu Trp Tyr Asp Cys Thr Trp Asn Thr Thr
         35                  40                  45

ACT CAA ACA TGG GCC TGC AGT AAC GTC AGT GAG AAT GGC TGG CTG AAG       192
Thr Gln Thr Trp Ala Cys Ser Asn Val Ser Glu Asn Gly Trp Leu Lys
     50                  55                  60

GCA GTG CAG GCC CTC ATG GTG CTG TCT CTC ATC CTC TGC TGC CTG TCC       240
Ala Val Gln Ala Leu Met Val Leu Ser Leu Ile Leu Cys Cys Leu Ser
 65                  70                  75                  80

TTC ATC CTC TTC ATG TTC CAA CTC TAC ACC ATG CGG CGC GGA GGG CTC       288
Phe Ile Leu Phe Met Phe Gln Leu Tyr Thr Met Arg Arg Gly Gly Leu
                 85                  90                  95

TTC TAC GCT ACC GGC CTC TGC CAG CTT TGC ACC AGT GCA GCT GTG TTC       336
Phe Tyr Ala Thr Gly Leu Cys Gln Leu Cys Thr Ser Ala Ala Val Phe
            100                 105                 110

TCC GGG GCA CTC ATC TAT GCC ATC CAC ACC GAG GAG ATC CTG GCC AAG       384
Ser Gly Ala Leu Ile Tyr Ala Ile His Thr Glu Glu Ile Leu Ala Lys
        115                 120                 125

CAC CCG AGT GGG GGC AGC TTC GGT TAC TGC TTC GCC CTG GCC TGG GTG       432
His Pro Ser Gly Gly Ser Phe Gly Tyr Cys Phe Ala Leu Ala Trp Val
    130                 135                 140

GCT TTT CCA CTC GCT CTG GTC AGC GGC ATT GTC TAC ATC CAC CTG CGG       480
Ala Phe Pro Leu Ala Leu Val Ser Gly Ile Val Tyr Ile His Leu Arg
145                 150                 155                 160

AAA CGT GAA TGA                                                       492
Lys Arg Glu  *
```

(2) INFORMATION FOR SEQ ID NO:4:

(i) SEQUENCE CHARACTERISTICS:
(A) LENGTH: 163 amino acids
(B) TYPE: amino acid
(D) TOPOLOGY: linear (ii) MOLECULE TYPE: protein (xi) SEQUENCE DESCRIPTION: SEQ ID NO:4:

```
Met Ser Leu Leu Leu Leu Val Val Ser Ala Leu His Ile Leu Ile Leu
  1               5                  10                  15

Val Leu Leu Phe Val Ala Thr Leu Asp Lys Ser Trp Trp Thr Leu Pro
             20                  25                  30

Asp Lys Glu Ser Leu Asn Leu Trp Tyr Asp Cys Thr Trp Asn Thr Thr
         35                  40                  45

Thr Gln Thr Trp Ala Cys Ser Asn Val Ser Glu Asn Gly Trp Leu Lys
     50                  55                  60
```

-continued

```
Ala Val Gln Ala Leu Met Val Leu Ser Leu Ile Leu Cys Cys Leu Ser
 65                 70                  75                  80

Phe Ile Leu Phe Met Phe Gln Leu Tyr Thr Met Arg Arg Gly Gly Leu
                85                  90                  95

Phe Tyr Ala Thr Gly Leu Cys Gln Leu Cys Thr Ser Ala Ala Val Phe
            100                 105                 110

Ser Gly Ala Leu Ile Tyr Ala Ile His Thr Glu Glu Ile Leu Ala Lys
        115                 120                 125

His Pro Ser Gly Gly Ser Phe Gly Tyr Cys Phe Ala Leu Ala Trp Val
    130                 135                 140

Ala Phe Pro Leu Ala Leu Val Ser Gly Ile Val Tyr Ile His Leu Arg
145                 150                 155                 160

Lys Arg Glu
```

(2) INFORMATION FOR SEQ ID NO:5:

(i) SEQUENCE CHARACTERISTICS:
(A) LENGTH: 160 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:5:

```
Met Leu Leu Leu Leu Leu Ser Ile Ile Val Leu His Val Ala Val Leu
1               5                   10                  15

Val Leu Leu Phe Val Ser Thr Ile Val Ser Gln Trp Ile Val Gly Asn
            20                  25                  30

Gly His Ala Thr Asp Leu Trp Gln Asn Cys Ser Thr Ser Ser Ser Gly
        35                  40                  45

Asn Val His His Cys Phe Ser Ser Ser Pro Asn Glu Trp Leu Gln Ser
    50                  55                  60

Val Gln Ala Thr Met Ile Leu Ser Ile Ile Phe Ser Ile Leu Ser Leu
65                  70                  75                  80

Phe Leu Phe Phe Cys Gln Leu Phe Thr Leu Thr Lys Gly Gly Arg Phe
                85                  90                  95

Tyr Ile Thr Gly Ile Phe Gln Ile Leu Ala Gly Leu Cys Val Met Ser
            100                 105                 110

Ala Ala Ala Ile Tyr Thr Val Arg His Pro Glu Trp His Leu Asn Ser
        115                 120                 125

Asp Tyr Ser Tyr Gly Phe Ala Tyr Ile Leu Ala Trp Val Ala Phe Pro
    130                 135                 140

Leu Ala Leu Leu Ser Gly Val Ile Tyr Val Ile Leu Arg Lys Arg Glu
145                 150                 155                 160
```

(2) INFORMATION FOR SEQ ID NO:6:

(i) SEQUENCE CHARACTERISTICS:
(A) LENGTH: 160 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:6:

```
Met Leu Leu Leu Leu Leu Gly Ile Leu Phe Leu His Ile Ala Val Leu
1               5                   10                  15
```

-continued

```
Val Leu Leu Phe Val Ser Thr Ile Val Ser Gln Trp Leu Val Gly Asn
            20                  25                  30

Gly His Thr Thr Asp Leu Trp Gln Asn Cys Thr Thr Ser Ala Leu Gly
        35                  40                  45

Ala Val Gln His Cys Tyr Ser Ser Ser Val Ser Glu Trp Leu Gln Ser
    50                  55                  60

Val Gln Ala Thr Met Ile Leu Ser Val Ile Phe Ser Val Leu Ala Leu
65                  70                  75                  80

Phe Leu Phe Phe Cys Gln Leu Phe Thr Leu Thr Lys Gly Gly Arg Phe
                85                  90                  95

Tyr Ile Thr Gly Phe Phe Gln Ile Leu Ala Gly Leu Cys Val Met Ser
            100                 105                 110

Ala Ala Ala Ile Tyr Thr Val Arg His Ser Glu Trp His Val Asn Thr
        115                 120                 125

Asp Tyr Ser Tyr Gly Phe Ala Tyr Ile Leu Ala Trp Val Ala Phe Pro
    130                 135                 140

Leu Ala Leu Leu Ser Gly Ile Ile Tyr Val Ile Leu Arg Lys Arg Glu
145                 150                 155                 160
```